United States Patent [19]

Dwyer et al.

[11] Patent Number: 5,238,689
[45] Date of Patent: Aug. 24, 1993

[54] USE OF RUTHENIUM RED AS IMMUNOSUPPRESSIVE AGENTS

[75] Inventors: Donard S. Dwyer, Lexington; Kristin Esenther, Ashland, both of Mass.

[73] Assignee: Procept, Inc., Cambridge, Mass.

[21] Appl. No.: 817,536

[22] Filed: Jan. 7, 1992

[51] Int. Cl.$^5$ .................... A01N 59/16; A61K 33/24
[52] U.S. Cl. .................... 424/617; 424/719
[58] Field of Search .................... 424/617, 719

[56] References Cited

PUBLICATIONS

Dornand et al, Biochemical Pharmacology 36 (22) 3929–3936, 1987.
Broekemeier et al, J. Biological Chem 264 (14) 7826–7830, 1989.
Kapus et al., J. of Biological Chemistry, 265 (30): 18063–18066 (1990).
Missiaen et al., Biochimica et Biophysica Acta, 1023:449–454 (1990).
Tsuro et al., Gann, 71: 151–154 (1980).

*Primary Examiner*—Marianne M. Cintins
*Assistant Examiner*—Rebecca Cook
*Attorney, Agent, or Firm*—Hamilton, Brook, Smith & Reynolds

[57] ABSTRACT

This invention relates to the use of Ruthenium Red as an immunosuppressive agent to prevent or significantly reduce graft rejection in organ and bone marrow transplantation. Ruthenium Red can also be used as an immunosuppressant drug for T lymphocyte mediated autoimmune diseases. Furthermore, Ruthenium Red may be useful in alleviating psoriasis.

5 Claims, 1 Drawing Sheet

USE OF RUTHENIUM RED AS IMMUNOSUPPRESSIVE AGENTS

BACKGROUND OF THE INVENTION

Replacement of defective or severely injured tissues and organs has been a medical objective as long as medicine has been practiced. Grafts from an individual to himself almost invariably succeed, and are especially important in the treatment of burn patients. Likewise, grafts between two genetically identical individuals almost invariably succeed. However, grafts between two genetically dissimilar individuals would not succeed without immunosuppressive drug therapies. The major reason for their failure is a T cell mediated immune response to cell-surface antigens that distinguish donor from host.

Immunosuppressive agents are also indicated in the treatment of autoimmune diseases such as rheumatoid arthritis or type I diabetes mellitus. One particular condition worth mentioning here is psoriasis. This disease is characterized by erythematous patches of skin accompanied by discomfort and itching. Herplasia of the epidermis is also a hallmark feature of psoriasis. An inflammatory component is suggested by: (i) the finding of lymphocytic infiltration of epidermis, and (ii) the fact that immunosuppressive agents such as cyclosporin and corticosteriods have beneficial effect on the disease.

A number of drugs are currently being used or investigated for their immunosuppressive properties. Among these drugs, the most commonly used immunosuppressant is cyclosporin A. However, usage of cyclosporin has numerous side effects such as nephrotoxicity, hepatotoxicity and other central nervous system disorders. Thus, there is presently a need to investigate new immunosuppressive agents that are less toxic but equally as effective as those currently available.

SUMMARY OF THE INVENTION

This invention relates to the use of Ruthenium Red as an immunosuppressive agent to prevent or significantly reduce graft rejection in organ and bone marrow transplantation. Ruthenium Red can also be used as an immunosuppressant drug for T lymphocyte mediated autoimmune diseases.

Other diseases with suspected inflammatory components, such as psoriasis, may also be amenable to treatment with Ruthenium Red.

BRIEF DESCRIPTION OF THE FIGURE

The FIGURE illustrates absorbance values obtained through an ELISA assay. The upper plot represents antibody levels in a group of mice treated with water, whereas the lower plot depicts the antibody levels for Ruthenium Red treated mice.

DETAILED DESCRIPTION OF THE INVENTION

Figure 1:
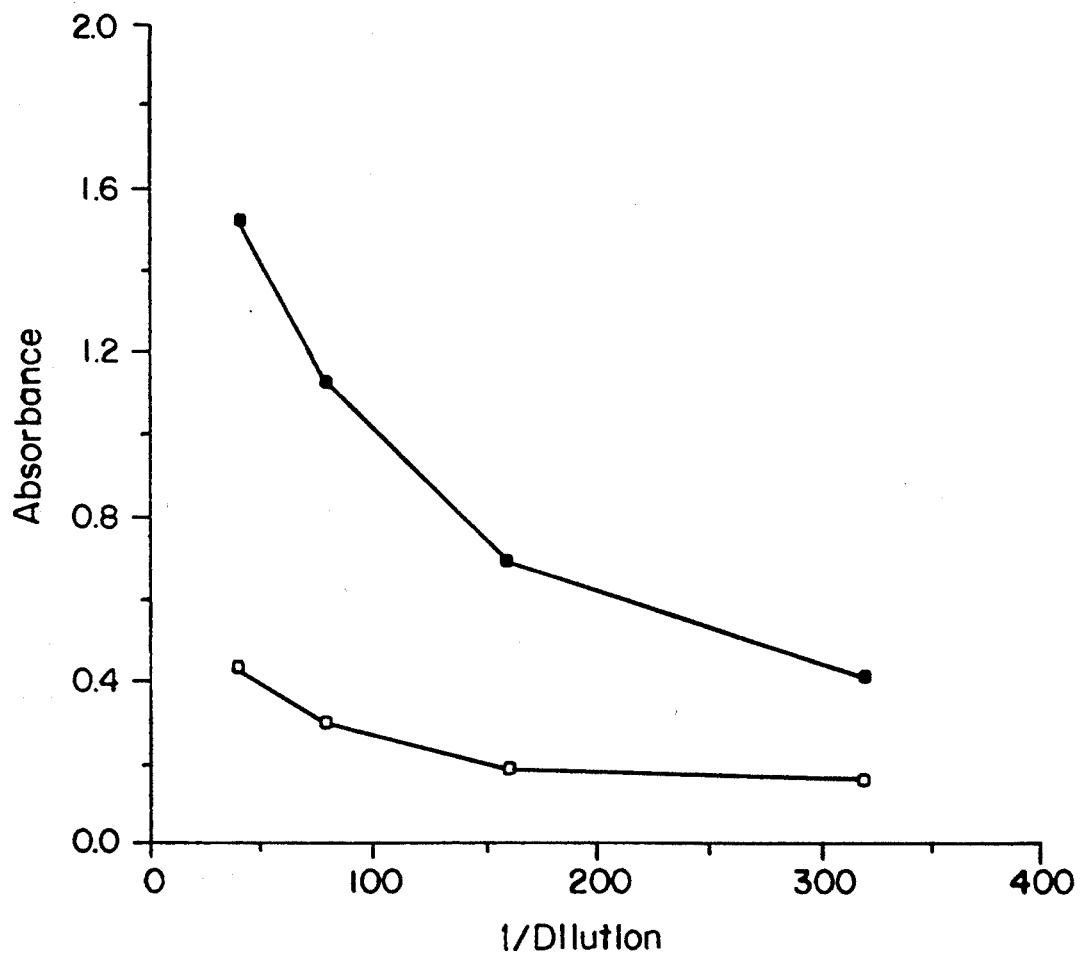

This invention is based upon the discovery that Ruthenium Red can inhibit T lymphocyte proliferation, and as such can be used as an immunosuppressant agent for organ rejection and transplantation or other conditions in which it is desirable to substantially reduce or suppress the immune system of an individual, such as T cell-mediated autoimmune diseases. Psoriasis, which exhibits certain features of an autoimmune disease or inflammatory condition, may be ideally suited for treatment with Ruthenium Red. Abnormalities in mitochondrial function in psoriatic epidermal cells may be corrected by Ruthenium Red which has known effects on mitochondria. Furthermore, the antiproliferative effects of this compound may reduce epidermal hyperplasia and, at the same time, diminish any contribution by T cells to the disease process. Topical application of Ruthenium Red in a cream or ointment could deliver locally high concentrations of the drug without significant systemic exposure. This may be the ideal treatment modality for psoriasis and perhaps other inflammatory skin disease, such as pemphigus vulgaris.

Ruthenium Red is an inorganic hexavalent polycationic dye that has been used in histology and electron microscopy to stain certain complex polysaccharides. These dyes have also been shown to affect calcium ion transport in the smooth muscle plasma membrane of pig stomach cells and in the mitochondria of rat liver cells. See Missiaen et al., *Biochimica et Biophysica Acta,* 1023:449–454 (1990) and Kapus et al., *J. of Biological Chemistry,* 265(30):18063–18066 (1990). In addition, Ruthenium Red has been shown to possess certain antitumor properties, as demonstrated by growth inhibition of Lewis lung carcinoma in mice treated with the dye. Tsuro et al., Gann, 71: 151–154 (1980).

It has now been discovered that Ruthenium Red possesses immunosuppressive activity as confirmed through a drug screen. Specific T cell proliferation was measured in response to antigen exposure in the presence or absence of Ruthenium Red. It was found that Ruthenium Red inhibited T cell proliferation by 50% ($IC_{50}$) at a concentration of about 200 nM. This compares favorably with cyclosporin A, which has an $IC_{50}$ at 15 nM. In an in vitro toxicity study, Ruthenium Red was found to be nontoxic to a variety of cell lines when tested at the same concentrations that markedly inhibit T cell activation.

The dye is known to bind a wide variety of materials, but more importantly, it binds to components of cell membranes. As previously mentioned, Ruthenium Red has been shown to inhibit $Ca^{2+}$ efflux. It is believed that the dye interacts at the cytoplasmic site of the $Ca^+$ pump; however, its mode of action is still not fully understood. It is known that $Ca^+$ is an important mediator of T cell activation. Transient elevation of cytoplasmic $Ca^{2+}$ occurs shortly after triggering of T cells by a variety of signals and is necessary for activation of the interleukin 2 (IL-2) gene. Recently, the immunosuppressive action of cyclosporin has been found to involve $Ca^{2+}$-dependent proteins which participate in gene activation. Ruthenium Red most likely effects the same signal transduction pathway as cyclosporin, but inhibits by either competing with $Ca^{2+}$ for key regulatory sites on proteins or by preventing the necessary rise in intracellular $Ca^{2+}$.

Ruthenium Red can be administered orally, parenterally (e.g. intramuscularly, intravenously, subcutaneously), topically, nasally or via slow releasing microcarriers in dosage formulations containing a physiologically acceptable vehicle and optional adjuvants and preservatives. Suitable physiologically acceptable vehicles include saline, sterile water, cream or ointments.

The specific dosage level of active ingredient will depend upon a number of factors, including biological activity of Ruthenium Red, age, body weight, sex, general health, severity of the particular disease to be treated and the degree of immune suppression desired. It should be understood that Ruthenium Red can be administered to mammals other than humans for immunosuppression of mammalian autoimmune diseases.

Ruthenium Red can be administered in combination with other drugs to boost the immunosuppressive effect. Compounds that can be co-administered include steroids (e.g. methyl prednisolone acetate) and known immunosuppressants such as azathioprine, 15-deoxyspergualin. Dosages of these drugs will also vary depending upon the condition and individual to be treated.

The assay used to measure T cell growth inhibition was a human peripheral blood lymphocyte (PBL) proliferation assay using a standard procedure known in the art. PBL's were chosen due to their known ability to proliferate in the presence of antigens derived from herpes simplex virus (HSV), Rubella or tetanus toxoid (TT). PBL growth inhibition was measured in terms of Ruthenium Red's ability to interfere with antigen induced lymphocyte proliferation.

The invention will be further illustrated by the following non-limiting Exemplification:

EXEMPLIFICATION

PBL Proliferation Assay

Ruthenium Red was purchased from Sigma Chemical Company, and dissolved in water at a 1 mg/ml concentration for the stock solution. The stock solution of the dye was diluted over a range of 1:400 to 1:100,000 for the PBL inhibition assay.

The lymphocytes were prepared by first separating them from the blood samples of several donors by Ficoll gradient separation as described by standard procedure known in the art. The isolated lymphocytes were then grown in RPMI 1640 medium containing 5% human AB serum, glutamine (2 mM), penicillin/streptomycin, 50 u/ml/50 ng/ml sodium pyruvate 1 mM and HEPES buffer 10 mM.

For assay purposes, PBL's were incubated at a density of $10^5$ per 200 μl of medium per well of a 96-well plate.

Concentrated tissue culture supernatants containing antigens derived from HSV infected cells were diluted 1:1000 to induce T cell proliferation.

In separate studies, Tetanus toxoid was used as a stimulating antigen at a concentration range of 0.4–4 LF/ml.; provided by Massachusetts Department of Public Health, Boston, Mass.

The test wells containing PBL's, were exposed to one of the three stimulating antigens (i.e. HSV, Rubella or TT derived antigens), along with various dilutions of the Ruthenium Red solutions, as shown in Table 1. The supernatant from uninfected cells (obtained from Microbix Biosystems, Inc. of Toronto, Canada) were used as a control.

Subsequently, HSV antigen/Ruthenium Red exposed PBL's were pulsed with 1 μCi/well of $^3$H-thymidine on day 4 whereas the Rubella/dye and TT/dye exposed cells were pulsed on day 5 using a standard procedure known in the art. The cells were then harvested 16 hours later onto a glass fiber filter using a PHD harvester from Cambridge Technology, Boston, Mass. Thymidine incorporation was measured by liquid scintillation counting using a Beta counter (Pharmacia, Inc., Piscataway, N.J.).

The results of the assay are shown in Table 1. The table shows that a 2.5 μg/ml concentration of Ruthenium Red generally inhibited proliferation by 90%. The molar concentration to obtain $IC_{50}$ was estimated to be approximately 200 nM. The inhibition values in Table 1 represent the means of 5 separate experiments.

TABLE 1

| Inhibition of human T cell proliferation by Ruthenium Red | |
|---|---|
| Concentration, μg/ml (μM) | % Inhibition |
| 2.5 (3.18) | 96 |
| 1.0 (1.27) | 89 |
| 0.2 (0.25) | 60 |
| 0.1 (0.13) | 31 |
| 0.01 (0.01) | 17 |

In addition, Ruthenium Red was shown to be non-toxic at levels effective as an immunosuppressant agent. Table 2 lists the cell-lines tested for toxicity.

TABLE 2

| Human cell lines used for toxicity assays | |
|---|---|
| Name | Description |
| Jurkat | T cell lymphoma |
| K562 | Erythroleukemia |
| Hs 294T | Melanoma Cells |
| U-937 | Monocytes from histiocytic lymphoma |
| M-EBV | Epstein-Barr virus-transformed B-cells |

To obtain a more complete picture of the range of responses effected by Ruthenium Red, the ability of this compound to inhibit alloreactivity was examined. A summary of these results is presented in Table 3.

TABLE 3

| Inhibition of alloreactivity by Ruthenium Red | |
|---|---|
| Concentration, μg/ml (μM) | % Inhibition |
| 2.5 (3.18) | 92 |
| 1.0 (1.27) | 85 |
| 0.2 (0.25) | 77 |
| 0.1 (0.13) | 69 |

Alloreactivity was measured by stimulating T cells from one donor with inactivated lymphocytes from a second donor. The inhibition values represent the means of 4 separate determinations. These data confirm that Ruthenium Red has broad immunosuppressive properties in vitro.

Moreover, it was discovered that the proliferative response induced directly in PBL's by IL-2 alone can be inhibited by this compound (Table 4). For these studies, human peripheral blood lymphocytes (PBL's) were incubated in vitro with varying concentrations of IL-2 and in the presence or absence of Ruthenium Red (0.2 μg/ml). After 3 days of culture, $^3$H-thymidine was added for 16 hr, cells were harvested, and the filters counted.

TABLE 4

| Ruthenium Red blocks IL-2-mediated T cell proliferation | | | |
|---|---|---|---|
| IL-2 (U/ml) | Ruthenium Red | $^3$H-thymidine uptake (cpm) | % Inhibition |
| 0 | — | 543 | — |
| 100 | — | 31,175 | — |
| 1 | — | 36,559 | — |
| 100 | + | 3,839 | 88 |
| 1 | + | 2,805 | 92 |
| 0.01 | + | 1,154 | 80 |

These findings suggest that Ruthenium Red cannot only prevent T cell activation (like cyclosporin) but can also abrogate the response to IL-2 which make this compound superior to cyclosporin.

In another study, T cells were activated with HSV-1 as described before and the Ruthenium Red (1 μg/ml) was added either at the start of culture (time 0) or after various delays. Data in Table 5 reveal that the compound can be added as late as 20 hours after triggering with antigen and still produce maximal inhibition, indicating that Ruthenium Red most likely effects signal transduction pathways rather than early recognition events at the cell surface.

TABLE 5

Kinetics of the inhibitory response to Ruthenium Red

| Time of addition (hr) | % Inhibition |
| --- | --- |
| 0 | 95 |
| 1 | 97 |
| 2 | 96 |
| 4 | 92 |
| 20 | 86 |
| 33 | 58 |

To uncover the mode of action of Ruthenium Red, additional experiments were performed. Because it is known that this compound effects $Ca^{2+}$ levels in cells, we examined whether Ruthenium Red prevents the rise in intracellular $Ca^{2+}$ that accompanies T cell activation. The $Ca^{2+}$-sensitive dye, Fluo-3AM (Molecular Probes, Inc., Eugene, Oreg.), can be used to detect intracellular $Ca^{2+}$. For these studies, transfected Jurkat T cells were incubated with Fluo-3AM (1 μM) for one hour at room temperature. The cells were then washed three times and incubated in 1 ml. volumes ($5 \times 10^5$ cells) with various agents to trigger T cell activation and thus $Ca^{2+}$ uptake. Ruthenium Red was added at a concentration of 1 μg/ml (1.27 μM).

The results in Table 6 show a major reduction in the percentage of cells staining positively with the dye, indicative of reduced levels of $Ca^{2+}$. Thus, Ruthenium Red prevents the rise in intracellular $Ca^{2+}$ in response to T cell activation.

TABLE 6

Calcium influx into activated human T cells is diminished by Ruthenium Red

| | Ruthenium Red | % Fluorescent cells |
| --- | --- | --- |
| Blank | — | 1.3 |
| Calcium ionophore | — | 84.6 |
| Activation (anti-CD2) | — | 47.0 |
| Activation (anti-CD2) | + | 17.2 |

Because the in vitro data appeared very promising, Ruthenium Red was tested for in vivo immunosuppressive properties. B10.A mice were treated with Ruthenium Red (dissolved in water) by intraperitoneal injection (4 mg/kg) daily for two days prior to immunization with cytochrome c (50 μg per mouse in complete Freund's adjuvant), and were treated for an additional 12 days after challenge with antigen. On day 23 after immunization, the animals were bled and sera were evaluated for specific antibodies to cytochrome c in an enzyme-linked immunosorbent assay (ELISA). The data are presented in FIG. 1. The absorbance values obtained in the ELISA have been plotted against the dilution of serum containing specific antibodies. The upper plot represents antibody levels in the group treated with water, whereas the lower plot depicts the ELISA values for the Ruthenium Red treated mice. Overall, treatment of mice with Ruthenium Red led to a 70% reduction in antibody levels when compared to the control mice who received water.

To extend these findings, the experiments were repeated with larger groups of mice and, in addition, the in vitro proliferative response of T cells to the immunizing antigen was evaluated. For these studies, B10.A mice were treated with Ruthenium RED as before and immunized with cytochrome c. On day 7 after challenge with antigen, draining lymph nodes were removed and single cell suspensions of lymphocytes were prepared. The lymphocytes were counted to estimate overall yields and were cultured in vitro with antigen (100 μg/ml) for three days prior to addition of tritiated thymidine to quantitate proliferation. The results are shown in Table 7.

TABLE 7

In vivo effects of Ruthenium Red on T cell responses of B10.A mice

| Mouse # | Ruthenium Red | Cell Yield | Specific proliferation (cpm) |
| --- | --- | --- | --- |
| 1 | — | $19 \times 10^6$ | 21,902 |
| 2 | — | $6.7 \times 10^6$ | 66,320 |
| 3 | — | $7 \times 10^6$ | 19,484 |
| 14 | + | $0.26 \times 10^6$ | nd |
| 16 | + | $0.81 \times 10^6$ | nd |
| 17 | + | $16 \times 10^6$ | 22,236 |

Mice treated with water exhibited normal enlargement of lymph nodes and on average yielded about $11 \times 10^6$ cells per mouse. In all cases, there was a good proliferative response to cytochrome c. In contrast, two of the three mice treated with Ruthenium Red showed no enlargement of lymph nodes following immunization and the total cell yields were 1/20th that observed in the controls. There were too few cells to assess T cell proliferation in vitro as indicated by 'nd' or not determined. The third mouse responded normally to cytochrome c.

The remaining mice in this study continued on their assigned treatment and were bled on day 23, as in the original pilot study, and sera were tested for specific antibodies in the ELISA. The data has been expressed as the mean of the endpoint dilution. The data have been summarized in Table 8.

TABLE 8

Ruthenium Red suppresses in vivo production of specific antibody

| Group | High Responders | Mean Titer |
| --- | --- | --- |
| Control | 8/9 | 40,106 ± 11,384 |
| Ruthenium Red | 2/6 | 18,613 ± 13,020 |

Mice were considered high responders if their antibody titer against cytochrome c was greater than 1:5,120.

The control mice produced high levels of antibody to cytochrome c; 8 of 9 had a titer greater than 1:5000. On the other hand, the mice treated with Ruthenium Red gave an inferior response; only 2 of the 6 mice had titers greater than 1:5000. These findings are in keeping with both the original pilot study and the in vitro proliferative data that suggested that two thirds of the mice show a greatly reduced response to antigen upon treatment with Ruthenium Red. Thus, the in vitro data demonstrating the immunosuppressive properties of Ruthenium Red have been confirmed by these in vivo studies.

Equivalents

Those skilled in the art will recognize, or be able to ascertain, using no more than routine experimentation many equivalents to the specific embodiments of the invention described herein. Such equivalents are intended to be encompassed by the following claims.

We claim:

1. A method of suppressing a T-lymphocyte mediates immune response of a mammal comprising administering to a mammal, a composition comprising an immunosuppressive amount of Ruthenium Red in a physiologically acceptable vehicle, wherein the T-lymphocyte mediated immune response is associated with a graft rejection.

2. The method of claim 1, further comprising administering the composition with an immunosuppressant selected from the group consisting of cyclosporin, rapamycin, FK-506, azathioprine and 15-deoxyspergualin.

3. The method of claim 1, wherein the mammal is a human.

4. A method of preventing or substantially reducing a T-lymphocyte mediate graft rejection in a mammal, comprising administering to the mammal a composition comprising an immunosuppressive amount of Ruthenium Red in a physiologically acceptable vehicle.

5. The method of claim 4, wherein the mammal is a human.

* * * * *

UNITED STATES PATENT AND TRADEMARK OFFICE
CERTIFICATE OF CORRECTION

PATENT NO. : 5,238,689

DATED : August 24, 1993

INVENTOR(S) : Donard S. Dwyer and Kristin Esenther

It is certified that error appears in the above-identified patent and that said Letters Patent is hereby corrected as shown below:

Claim 1, Column 7, line 11, delete "mediates" and insert
---mediated---.

Claim 4, Column 8, line 10, delete "mediate" and insert
---mediated---.

Signed and Sealed this

Twenty-third Day of August, 1994

Attest:

BRUCE LEHMAN

Attesting Officer   Commissioner of Patents and Trademarks